United States Patent [19]

Beuther et al.

[11] Patent Number: 4,605,680
[45] Date of Patent: Aug. 12, 1986

[54] CONVERSION OF SYNTHESIS GAS TO DIESEL FUEL AND GASOLINE

[75] Inventors: Harold Beuther, Cheswick; Charles L. Kibby, Gibsonia; Thaddeus P. Kobylinski, Prospect; Richard B. Pannell, Allison Park, all of Pa.

[73] Assignee: Chevron Research Company, San Francisco, Calif.

[21] Appl. No.: 768,923

[22] Filed: Aug. 23, 1985

Related U.S. Application Data

[63] Continuation of Ser. No. 301,973, Oct. 13, 1981, abandoned.

[51] Int. Cl.$^4$ .............................................. C07C 1/04
[52] U.S. Cl. ................................. 518/715; 502/302; 585/322
[58] Field of Search ............... 518/715; 585/419, 322; 44/54

[56] References Cited

U.S. PATENT DOCUMENTS

| | | |
|---|---|---|
| 2,284,468 | 5/1942 | Burk et al. |
| 2,463,875 | 3/1949 | Hibshman |
| 2,471,914 | 5/1949 | Sweetser |
| 2,548,159 | 4/1950 | Houtman |
| 2,785,209 | 3/1957 | Schmetterling |
| 3,536,632 | 10/1970 | Kroll |
| 4,043,944 | 1/1977 | Juguim et al. |
| 4,193,895 | 3/1980 | Light |
| 4,201,661 | 5/1980 | Juguim et al. |

*Primary Examiner*—Howard T. Mars
*Attorney, Agent, or Firm*—Roylance, Abrams, Berdo & Goodman

[57] ABSTRACT

Synthesis gas is converted to diesel fuel and a high octane gasoline in two stages. In the first stage the synthesis gas is converted to straight chain paraffins mainly boiling in the diesel fuel boiling range utilizing a catalyst consisting essentially of cobalt, preferably promoted with a Group IIIB or IVB metal oxide, on a support of gamma-alumina, eta-alumina or mixtures thereof. A straight chain paraffin portion of the effluent in the $C_5$–$C_9$ range is converted in a second stage to a highly aromatic and branched chain paraffinic gasoline using a platinum group metal catalyst.

30 Claims, No Drawings

CONVERSION OF SYNTHESIS GAS TO DIESEL FUEL AND GASOLINE

This is a continuation of application Ser. No. 310,973 filed Oct. 13, 1981 now abandoned.

FIELD OF THE INVENTION

This invention relates to a process for the synthesis of diesel fuel and gasoline from CO and hydrogen. More particularly, this invention relates to a plural stage conversion of synthesis gas to diesel fuel in a first stage, and to dehydrocyclization of a naphtha stream produced in the first stage to gasoline in a second stage.

BACKGROUND OF THE INVENTION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons by the catalyzed reaction of CO and hydrogen. Commercial plants have operated in Germany, South Africa and other parts of the world based on the use of particular catalysts. The German commercial operation, for example, concentrated on the use of a precipitated cobalt-thoria-kieselguhr fixed-bed catalyst, and a later modification where MgO, for economy reasons, replaced part of the thoria.

More recently, U.S. Pat. No. 4,088,671 to T. P. Kobylinski describes the use of a ruthenium promoted cobalt catalyst on a support, such as alumina or kieselguhr, in the synthesis of hydrocarbons from the reaction of CO and hydrogen at substantially atmospheric pressure. It was found that the addition of small amounts of ruthenium to a cobalt synthesis catalyst resulted in the substantial elimination of methane from the product, together with the production of a more saturated, higher average carbon number product. Likewise, catalyst comprising cobalt-thoria-MgO on an alumina or kieselguhr support is described in British Pat. No. 1,548,468 to Bijwaard et al for use in the Fischer-Tropsch synthesis of hydrocarbons.

SUMMARY OF THE INVENTION

It has now been found in accordance with the present invention, that synthesis gas consisting essentially of CO and hydrogen can be selectively converted to high cetane diesel fuel and high octane gasoline in two stages, by the steps of (A) selectively converting synthesis gas to a product high in straight chain paraffins in the diesel fuel boiling range ($C_9$–$C_{21}$) using a catalyst consisting essentially of cobalt, preferably promoted with an oxide of a metal of either Group IIIB or IVB of the Periodic Chart of the Elements, on a high purity, high surface area, low acidity support consisting essentially of gamma-alumina, eta-alumina or mixtures thereof, and (B) subjecting a stream comprising straight chain paraffins in the $C_5$–$C_9$ range produced in stage (A) to dehydrocyclization in the presence of a platinum group metal catalyst, to produce a high octane gasoline boiling range product.

The process of the present invention enables the production of both high cetane diesel fuel and high octane gasoline in amounts depending upon the conditions and particular catalysts utilized. In this way, the respective amounts of diesel fuel and gasoline can be varied to meet consumer demands.

DESCRIPTION OF THE PREFERRED EMBODIMENTS

Preferably, the synthesis gas consisting essentially of CO and hydrogen is converted under conditions and with a catalyst suitable to provide a major portion of high cetane diesel fuel and a lesser amount of paraffinic hydrocarbons in the $C_5$–$C_9$, preferably $C_6$–$C_8$ boiling range. A suitable catalyst system for the first stage of the process of the present invention is described in U.S. application Ser. No. 310,969, entitled "Conversion of Synthesis Gas to Diesel Fuel and Catalyst Therefor" in the name of Beuther, H., Kobylinski, T. P., Kibby, C. L. and Pannell, R. B., the disclosure of which is hereby incorporated by reference.

Thus, the catalyst utilized in the synthesis gas conversion stage of the present invention consists essentially of cobalt preferably promoted with a Group IIIB or Group IVB metal oxide, on gamma or eta-alumina or mixtures thereof having low acidity, high surface area and high purity.

Any suitable Group IIIB or IVB metal oxide can be employed in the first stage catalyst of the present invention, with oxides of the actinides and lanthanides being preferred. Thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lu_2O_3$, $UO_2$, $UO_3$, $U_3O_8$, $UO_4 \cdot 2H_2O$, and the like. Especially preferred metal oxides for inclusion in the catalyst of the present invention include $ThO_2$, $La_2O_3$, $CeO_2$, $ZrO_2$, $TiO_2$, $HfO_2$, and unseparated rare earth oxide mixtures high in lanthanum, praseodynium, and neodynium. The most preferred metal oxide for use in the catalyst of the present invention is thoria and reference will be hereinafter made thereto for example.

The alumina support is either gamma-alumina or eta-alumina or mixtures thereof characterized as having low acidity, a high surface area and high purity. The expression "low acidity" as used in the present application means that the present alumina support has a Brønsted acidity with $H_o \leq 1.5$ which is less than 5 micromol per gram or about $10^{16}$ acid sites per m² of surface area. The low acidity of the support of the present invention is required in order to enable the catalyst to provide a high molecular weight hydrocarbon product boiling in the diesel fuel range.

The synthesis gas conversion catalyst of the present invention has a hydrogen chemisorption value of at least 100, preferably from about 125 to about 300 especially 150 or 200 to 300 micromol hydrogen per gram of total catalyst when measured at 25° C., which values are substantially higher than achieved using an aqueous impregnation solution containing similar metals.

The surface area of the alumina support of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram.

As indicated, the catalyst support of the present invention must be of high purity. The expression "high purity" as used in the present application means that the catalyst contains negligible amounts of sodium, sulphate, silicon, phosphates or other material having a deleterious effect on the metal dispersion or the production of high molecular weight hydrocarbon products. For impurities creating acid sites, less than 5 micromol per gram should be present (about 0.01-0.1 weight percent depending on molecular weight). The deleterious effect of acidity is isomerization and cracking of intermediate olefins, removing them from chain growth and producing a low molecular weight product.

Unlike the catalyst described in U.S. Pat. No. 4,088,671 to Kobylinski, the catalyst of the present invention does not require ruthenium to increase the average molecular weight of the hydrocarbon products. Thus, the catalyst of the present invention contains no ruthenium.

Thus, the synthesis gas conversion catalyst of the present invention can contain the Group IIIB or IVB metal oxide, e.g. thoria, in amounts of from 0 or about 0.05 to about 100 parts by weight per 100 parts by weight cobalt, preferably from about 0.5 to 25 parts per 100 parts cobalt, with from about 1 to about 10 parts by weight per 100 parts by weight cobalt being especially preferred. The relatively low levels of the Group IIIB or IVB metal oxide control residual catalyst impurities. Thus, such component can be omitted and the catalyst is still operative. In order to omit the Group IIIB or IVB metal oxide from the catalyst, it is merely omitted from the impregnation solution.

The alumina support which is composed of gamma-alumina, eta-alumina or mixtures thereof is present in an amount of from about 10 to about 10,000 parts by weight alumina per 100 parts by weight of cobalt, preferably between about 100 and about 2,000 parts of alumina per 100 parts of cobalt, with from about 200 to about 400 parts by weight of alumina per 100 parts by weight cobalt being especially preferred. Pure gamma-alumina is preferred.

The method employed to deposit the catalytic metals of the present invention onto the alumina support involves the use of a nonaqueous, organic impregnation solution consisting essentially of a soluble cobalt salt and a soluble Group IIIB or IVB salt i.e., thorium salt, in order to achieve the necessary metal loading and distribution required to provide the highly selective and active catalyst of the present invention.

Initially, the alumina support is treated by oxidative calcination of the gamma and/or eta-alumina at a temperature in the range of from about 300° to about 800° C., preferably from about 400° to about 600° C.

Meanwhile, a nonaqueous organic solvent solution of the cobalt and thoria salts is prepared. The nonaqueous organic solvent of the present invention is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents include, for example, ketones, such as acetone, butanone (methyl ethyl ketone); the lower alcohols, e.g., methanol, ethanol, propanol and the like; amides, such as dimethyl formamide; amines, such as butylamine; ethers, such as diethylether; hydrocarbons, such as pentane and hexane; and mixtures of the foregoing solvents.

The preferred solvent of the present invention is a mixture of ethanol and acetone, for example, in a weight ratio of about four parts acetone per part of ethanol.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

Suitable cobalt salts include, for example, cobalt nitrate, cobalt acetate, cobalt carbonyl, cobalt acetylacetonate, or the like with cobalt nitrate and cobalt carbonyl [$Co_2(CO)_8$] being especially preferred. Likewise, any suitable Group IIIB or Group IVB metal salt, such as thorium nitrate, thorium acetate or the like can be employed. In general, any metal salt which is soluble in the organic solvent of the present invention and will not introduce acidity or have a poisonous effect, e.g. a halide, on the catalyst can be utilized. Thorium nitrate is especially preferred.

Next, the calcined alumina support is impregnated in a dehydrated state with the non-aqueous, organic solvent solution of the cobalt and thorium salts. Thus, the calcined alumina should not be unduly exposed to atmospheric humidity so as to become rehydrated.

Any suitable impregnation technique can be employed including techniques well known to those skilled in the art so as to distend the catalytic metals in a uniform thin layer on the catalyst support. For example, the cobalt and thoria can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess solvent present, e.g., ethanol and acetone is merely removed by evaporation. Thus, the impregnation solution can be added in excess, namely, up to five times the pore volume of the alumina, or can be added using just enough solution to fill the pore volume of the alumina.

Next, the impregnation solution and alumina are stirred while evaporating the solvent at a temperature of from about 25° to about 45° C. until "dryness".

If additional impregnations are needed to obtain the desired metal loading, for example, when the incipient wetness technique is used, the dried catalyst is then calcined in the presence of an oxygen-containing or inert, e.g. nitrogen, gas at a temperature just sufficient to decompose the metal salts and fix the cobalt. Suitable calcination temperatures include those in the range of from about 150° to about 300° C., preferably from about 225° to about 275° C. Such impregnation, drying and calcination can be repeated until the desired metal loading is achieved. If cobalt carbonyl is employed, contact with oxygen must be avoided. Thus, the impregnated catalyst is heated to about 200° C. in an inert gas, e.g., nitrogen, or hydrogen rather than using an oxidative calcination step.

After the last impregnation sequence, the impregnated catalyst is preferably slowly reduced in the presence of hydrogen. The reduction is best conducted in two steps wherein the first reduction heating step is carried out at a slow heating rate of no more than from about 0.5° to about 5° C. per minute, preferably from about 0.5° to about 1° C. per minute up to a maximum hold temperature of 180° to about 220° C., preferably 190° to about 210° C., for a hold time of from about 6 to about 24 hours, preferably from about 16 to about 24 hours. In the second reduction heating step, the catalyst can be heated at from about 5° to about 20° C. per minute, preferably from about 5° to about 10° C. per minute to a maximum hold temperature of from about 250° or 300° up to about 400° C., preferably from about 350° to about 400° C. for a hold time of 6 to about 65 hours, preferably from about 16 to about 24 hours. Although pure hydrogen can be employed for this reduction step, a mixture of hydrogen and nitrogen can be utilized in order to slowly reduce the catalyst. For example, the reduction step can be conducted initially using a gaseous mixture comprising 5% hydrogen and 95% nitrogen, and thereafter, the concentration of hydrogen can be gradually increased until pure hydrogen is obtained so as to slowly reduce the catalyst. Such slow reduction is particularly desirable when the metal salts utilized in the impregnation step are nitrates so as to avoid the dangers involved with an exothermic reaction in which nitrates are given off. Thus, the slow reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Such slow reduction process is not required when the cobalt salt is not a nitrate, e.g. cobalt acetate. A zero valent cobalt compound such as cobalt carbonyl can be activated by heating to 200° C. in pure hydrogen overnight.

It is preferred to omit the calcination step following the last impregnation and subject the impregnated catalyst directly to the slow reduction process.

The catalyst of the present invention has an average particle diameter which depends upon the type of reactor used of from about 0.01 to about 6 millimeters; preferably from about 1 to about 6 millimeters for a fixed bed; preferably about 0.02 to about 0.15 being preferred for a fluidized bed and from about 0.01 to about 0.05 millimeters for a slurry.

The charge stock used in the first stage of the process of this invention is a mixture of CO and hydrogen. The source of the CO and hydrogen to be used in the charge stocks for this invention is not critical and can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed.

The molar ratio of hydrogen to CO in the charge stock can be, for example, from about 0.5:1 to about 4:1 or higher, e.g., 10:1, preferably, from about 1:1 to about 2.5:1, with 1.5:1 to about 2:1 being especially preferred.

The reaction temperature is suitably from about 160° to about 350° C., preferably from about 175° to about 250° C., and most preferably from about 185° to about 215° C. The total pressure is from about 1 to about 100 atmospheres, preferably from about 1 to about 50 atmospheres, and most preferably from about 1 to about 20 atmospheres. The hydrogen partial pressure is from about 0.1 to about 30 atmospheres, preferably from about 0.5 to about 25 atmospheres, and most preferably from about 1 to about 20 atmospheres.

The gaseous hourly space velocity based upon the total amount of feed is less than 20,000 volumes of gas per volume of catalyst per hour, preferably from about 100 to about 5,000 v/v/hour, with from about 200 to about 2,500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The synthesis gas reaction using the catalysts of this invention can occur in a fixed, fluid or moving bed type of operation, and the type of operation would not appear to be critical. However, a fixed-bed operation is preferred, and normally the charge gases would be passed downflow through the bed of catalyst and the reaction product would be collected by suitable condensation techniques, after which the products can be separated by fractionation or otherwise.

Next, the effluent from the synthesis gas reaction stage is passed to a fractionator, which can be, for example a single or a multistage vapor-liquid fractionator operated at atmospheric pressure or under a vacuum so as to separate the first stage effluent into preferably a $C_9+$ fraction which is recovered as diesel fuel.

The feed to the dehydrocyclization stage comprises normal $C_5$-$C_9$ paraffins and olefins with small quantities of isoparaffins and isoolefins, but is preferably a $C_6$-$C_8$ fraction. The charge stock is contacted with a dehydrocyclization catalyst to convert such fraction to a highly aromatic and branched chain paraffinic high octane gasoline product.

Suitable catalysts include platinum group metals, e.g., iridium, osmium, palladium, ruthenium, rhodium, platinum, in amounts, for example, from about 0.1 to about 0.6 weight percent, preferably from about 0.15 to about 0.5 weight percent, based upon total catalyst weight. The catalyst can be promoted with between about 0.01 and about 1 percent by weight of the total catalyst of a metal such as ruthenium, tin, palladium, rhodium, rhenium, iridium, germanium, lead or the like. Preferably, 0.1 to about 0.5 weight percent promoter is utilized based on the total catalyst weight. In addition, the catalyst preferably contains a halogen, e.g., chlorine, fluorine, bromine, iodine, in an amount of from about 0.01 to about 1.0 weight percent, preferably from about 0.1 to about 0.5, especially 0.05 to about 0.5 weight percent based on total catalyst weight. The halogen, preferably chlorine, is supplied to the catalyst as a halogen salt of the platinum group metal and/or its promotor. Preferably, the amount of halogen is a maximum of six mols of halogen per mol of platinum group metal and/or metal promotor in the catalyst, excluding support metal. Any suitable support can be utilized. However, a low acidity aluminum support, such as the gamma-alumina and/or eta-alumina, utilized in the first stage of the process of the present invention is preferred. The lower acidity gamma-alumina is most preferred. An especially preferred catalyst is platinum promoted with iridium on a gamma-alumina support. The catalyst can be prepared in any suitable manner. Any suitable metal salt or metal compound can be used to prepare the impregnation solution. Halogen salts are preferred. Suitable halogen metal salts include for example, dihydrogen hexachloroplatinate, dihydrogen hexabromoplatinate, dihydrogen hexachloroiridate, dihydrogen hexabromoiridate. Additionally, the catalyst metals can be supplied to the catalyst by means of a non-halogen compound, such as an organometallic compound, e.g., platinum 2,4-pentanedionate and iridium-carbonyl. Salts of the platinum group metal and promoter can be coimpregnated on the alumina support using an impregnation solvent, such as that described in connection with the first stage catalyst preparation. Preferably, the solvent comprises, water, methanol, propanol, isopropanol, acetone, or water and ethanol in a ratio of from about 10:1 to about 1:1, preferably from about 3:1 to about 6:1 in amounts at least sufficient to fill the catalyst pore volume up to about 5 times said amount. Next, the catalyst is dried, preferably in air at a temperature of between about 20° to about 150° C., preferably from about 25° to about 60° C., and thereafter activated in hydrogen by increasing the ambient temperature to 375° C. at 5° C. per minute, for example. Preferably, the catalyst is not calcined. Thus, after impregnation, the catalyst is just dried for removal of solvent, reduced and then placed on stream.

Suitable reaction conditions include temperatures in the range of from about 370° to about 550° C., preferably from about 425° to about 500° C. Reaction pressures are, for example, from about 0 to about 500 psi, preferably from about 100 to about 300 psi. Hydrogen is fed to the dehydrocyclization reaction zone in amounts sufficient to provide a ratio of hydrogen to hydrocarbon charge stock of from about 0.25:4, preferably 0.5 to about 2 mols of hydrogen per mol of hydrocarbon.

The gaseous hourly space velocity based upon the total amount of feed is from about 0.1 to about 4, preferably 0.5 to about 2 on a weight hourly space velocity basis (WHSV).

The invention will be further described with reference to the following experimental work.

EXAMPLE 1

A cobalt catalyst component (B) was made by impregnating pure gamma-alumina (commercially available from Ketjen as CK-300) that had been sieved to pass 100 mesh (0.15 millimeter) and calcined for two hours at 600° C., by a single step, nonaqueous, "wet" impregnation using cobalt nitrates [$Co(NO_3)_2 6H_2O$] and thorium nitrates [$Th(NO_3)_4 4H_2O$] from acetone-ethanol solution in a ratio of acetone/ethanol of approximately 2.5:1. Excess solvent was removed by evaporation at a reduced pressure of approximately 0.01 atmosphere and 25°–30° C. in a rotary evaporator. The catalyst was dried at a temperature of 90° C. with moderate stirring. Melting of the nitrate salts and evolution of water occurred at approximately 50°–60° C. After the water had evolved, the catalyst appeared to be dry.

Prereduction and passivation of the impregnated catalyst was conducted using pure hydrogen at the rate of 720 cm$^3$/gram/hour. The impregnated catalyst was heated to 100° C. at the rate of 5° C. per minute and then maintained at that temperature for about one hour. Next, the catalyst was heated at the rate of 5° C. per minute to a temperature of 200° C. and then held at 200° C. for approximately sixteen hours. The catalyst was then heated at the rate of 10° C. per minute until a temperature of 360° C. was reached and then held at that temperature for twenty-two hours. Next, the catalyst was cooled to below 200° C., purged with nitrogen and further cooled. Air was bled into the nitrogen flow at approximately 1 cubic centimeter of air in 50 cubic centimeters of nitrogen per minute per 5 grams of catalysts for a period of sixteen hours.

The resultant catalyst contained 100 parts by weight cobalt, 18 parts by weight thoria and 200 parts by weight alumina ($100Co/18ThO_2/200Al_2O_3$). In order to determine cobalt dispersion, hydrogen chemisorption was measured after reduction at 50° C. intervals, from 200° C. to 400° C., for 16 hours at 175 cm$^3$ H$_2$/gram/hour. The chemisorption isotherms were measured at 25° C. after a one hour equilibration at a H$_2$ pressure of about 500 torr (65 kPa); the zero pressure intercept extrapolated from data points above 100 torr was taken as the amount chemisorbed. The results are shown in Table I:

TABLE I

| Hydrogen Sorbed at 25° C.[1] (micromol per gram) | | | | | |
|---|---|---|---|---|---|
| Reduction Temperature, °C. | | | | | H/Co |
| 200 | 250 | 300 | 350 | 400 | (350° C. Reduction) |
| 51 | 96 | 154 | 176 | 148 | .066 |

[1]Intercept values for 100–500 mm Hg data, based on weight of reduced catalyst.

The greatest sorption capacity was developed at 350° C. Assuming complete reduction at that temperature, and one hydrogen atom per surface cobalt atom, the values in the last column of Table I estimate the cobalt metal dispersion.

EXAMPLES 2–6

A series of runs were conducted using the catalyst of Example 1 ($100Co/18ThO_2/200Al_2O_3$) having an average particle size of about 0.4–0.6 millimeter wherein 0.5 gram samples of the prereduced catalyst were initially heated to a temperature of 360° C. in chemically pure hydrogen flowing at the rate of 2400–6000 cm$^3$/gram/hour at the rate of 5° C. per minute for a one hour period, and then held for 65 hours at 360° C.

The hydrogen flow was then reduced to 240 cm$^3$/gram/hour and an equal flow of carbon monoxide was initiated. For those runs where the molar ratio of hydrogen/CO is 2:1, the hydrogen flow rate was increased to 480 cm$^3$/gram/hour.

Sampling was conducted periodically to analyze the products. The conditions utilized in each run and the product distribution is set forth in Table II:

TABLE II

| Ex. No. | 2 | 3 | 4 | 5[2] | 6[3] |
|---|---|---|---|---|---|
| Temp., °C. | 175 | 185 | 195 | 205 | 195 |
| H$_2$/CO | 1:1 | 1:1 | 1:1 | 1:1 | 2:1 |
| CO Flowrate (cm$^3$/gram/hour) | 155 | 155 | 270 | 610 | 270 |
| CO Conversion Rate (cm$^3$/gram/hour) | | | | | |
| To CO$_2$ | 0.2 | 1.1 | 1.6 | 2.9 | (1.3) |
| To Hydrocarbons | 19 | 41 | 61 | 79 | (120) |
| CO Conversion (Percent) | 13 | 27 | 23 | 13 | 44 |
| Product Distribution (Carbon Atom %) | | | | | |
| CH$_4$ | 4 | 5 | 6 | 8 | 9 |
| C$_2$—C$_4$ | 6 | 7 | 8 | 10 | 9 |
| C$_5$—C$_8$ | 23 | 25 | 29 | 34 | 24 |
| C$_9$—C$_{20}$ | 62 | 59 | 50 | 44 | 49 |
| C$_{21}$+ | 5 | 4 | 7 | 4 | 9 |

[2]Separate run
[3]Not aged at 205° C.

The results set forth in Table II indicate that the cobalt catalyst component B has good activity and has a high degree of selectivity to C$_9$–C$_{20}$ hydrocarbons in the 50–65% range when the temperature is from 175°–195° C.

EXAMPLE 7

A charge stock containing equal molar quantities of n-hexane, n-heptane and n-octane simulating the $C_6$–$C_8$ byproduct fraction from Examples 2–6 was passed over a catalyst containing 0.3 weight percent platinum, 0.2 weight percent iridium and 0.5 weight percent chlorine supported on gamma-alumina. The foregoing weight percents are based upon the total catalyst weight. The charge stock was contacted with the catalyst at a temperature of 470° C. under a hydrogen pressure of 150 psi and a weight hourly space velocity of 1.0 using a hydrogen to hydrocarbon molar ratio of 2:1.

The resulting gasoline boiling range product had an octane number of 96 and an aromatics content of 29 weight percent based on liquid yield.

EXAMPLE 8

A charge stock containing equal molar quantities of n-hexane, n-heptane and n-octane simulating the $C_6$–$C_8$ byproduct fraction from Examples 2–6 was passed over a catalyst containing 0.375 weight percent platinum, 0.375 weight percent rhenium and 1.0 weight percent chlorine supported on gamma-alumina prepared using an aqueous impregnation. The foregoing weight percents are based upon the total catalyst weight. The charge stock was contacted with the catalyst at a temperature of 470° C. under a hydrogen pressure of 70 psi and a weight hourly space velocity of 1.0 using a hydrogen to hydrocarbon molar ratio of 2:1.

The resulting gasoline boiling range product had an octane number of 30 and an aromatics content of 11.0 weight percent based on liquid yield.

EXAMPLE 9

A charge stock containing n-heptane was passed over a catalyst containing 0.3 weight percent platinum, 0.2 weight percent iridium and 0.50 weight percent chlorine supported on gamma-alumina prepared using a water-ethanol impregnation solution. The foregoing weight percents are based upon the total catalyst weight. The charge stock was contacted with the catalyst at a temperature of 470° C. under a hydrogen pressure of 70 psi and a weight hourly space velocity of 1.0 using a hydrogen to hydrocarbon molar ratio of 2:1.

The resulting gasoline boiling range product had an aromatics content of 82.6 weight percent based on liquid yield.

EXAMPLE 10

For comparative purposes, the procedure of Example 9 using an n-heptane charge stock was repeated using a catalyst containing 0.375 weight percent platinum, 0.375 weight percent rhenium and 1.0 weight percent chlorine supported on gamma-alumina prepared using an aqueous impregnation. The foregoing weight percents are based upon the total catalyst weight. The charge stock was contacted with the catalyst at a temperature of 470° C. under a hydrogen pressure of 150 psi and a weight hourly space velocity of 1.0 using a hydrogen to hydrocarbon molar ratio of 2:1.

The resulting gasoline boiling range product had an aromatics content of 64.0 weight percent based on liquid yield.

EXAMPLE 11

The procedure of Example 9 using an n-heptane charge stock was repeated with a catalyst containing 0.375 weight percent platinum, 0.11 weight percent ruthenium and 0.50 weight percent chlorine supported on gamma-alumina prepared using an aqueous impregnation. The foregoing weight percents are based upon the total catalyst weight. The charge stock was contacted with the catalyst at a temperature of 470° C. under a hydrogen pressure of 150 psi and a weight hourly space velocity of 1.0 using a hydrogen to hydrocarbon molar ratio of 2:1.

The resulting gasoline boiling range product had an aromatics content of 73.0 weight percent based on liquid yield.

What is claimed is:

1. A process for the conversion of synthesis gas to diesel fuel and gasoline, which comprises contacting synthesis gas consisting essentially of CO and hydrogen in a synthesis gas conversion zone with a synthesis gas conversion catalyst comprising cobalt and 0 to about 100 parts by weight of a Group IIIB or IVB metal oxide per 100 parts by weight of said cobalt, on a high surface area, high purity, low acidity alumina support of gamma-alumina, eta-alumina or mixtures thereof, said catalyst having a hydrogen chemisorption value of from about 100 to about 300 micromol of hydrogen per gram of total catalyst when measured at 25° C., said catalyst having been prepared by (A) impregnation of said alumina support with a non-aqueous, organic solvent impregnation solution of cobalt nitrate and (B) reduction of said impregnated alumina support by heating, in the presence of hydrogen gas, at a heating rate of from about 0.5° to about 5° C. per minute to a maximum hold temperature in the range of 180° to about 220° C. for a hold time of 6 to about 24 hours and thereafter heating said impregnated alumina support in the presence of hydrogen gas while heating up to a maximum hold temperature of from about 250° to about 400° C. for a hold time of 6 to about 65 hours, to produce a reaction effluent comprising straight chain hydrocarbons boiling in the diesel fuel boiling range and in the $C_5$–$C_9$ range, separating a stream comprising said straight chain paraffins in the $C_5$–$C_9$ range from the reaction effluent and subjecting said separated stream to dehydrocyclization in the presence of hydrogen and a dehydrocyclization catalyst in a dehydrocyclization conversion zone to produce a high octane gasoline product.

2. The process of claim 1 wherein said separated stream comprises straight chain paraffins boiling in the $C_6$–$C_9$ range.

3. The process of claim 1 wherein said dehydrocyclization catalyst comprises a low acidity catalyst supported on gamma-alumina, eta-alumina, or mixtures thereof.

4. The process of claim 1 wherein said dehydrocyclization is conducted using a catalyst consisting essentially of a promoted platinum group metal.

5. The process of claim 2 wherein said dehydrocyclization catalyst is platinum promoted with a platinum group metal.

6. The process of claim 5 wherein said promoter is iridium.

7. The process of claim 5 wherein said dehydrocyclization catalyst is additionally promoted with a halogen.

8. The process of claim 7 wherein said halogen is chlorine.

9. The process of claim 1 wherein said dehydrocyclization is conducted at a temperature in the range of from about 370° to about 550° C.

10. The process of claim 1 wherein the ratio of hydrogen to hydrocarbon in said dehydrocyclization conversion zone is from about 0.25:1 to about 4:1.

11. The process of claim 1 wherein said synthesis gas conversion catalyst contains from about 0.05 to about 100 parts by weight Group IIIB or IVB metal oxide per 100 parts by weight cobalt.

12. The process of claim 11 wherein said synthesis gas conversion catalyst contains from about 1 to about 10 parts by weight Group IIIB or IVB metal oxide per 100 parts by weight cobalt.

13. The process of claim 11 wherein said metal oxide is an oxide of an actinide, a lanthanide or zirconium.

14. The process of claim 13 wherein said metal oxide is thoria.

15. The process of claim 13 wherein said metal oxide is lanthana.

16. The process of claim 1 wherein said synthesis gas conversion catalyst support is gamma-alumina.

17. The process of claim 1 wherein the molar ratio of hydrogen to CO in said synthesis gas conversion zone is from about 0.5:1 to about 4:1.

18. The process of claim 17 wherein the molar ratio of hydrogen to CO is from about 1:1 to about 2.5:1.

19. The process of claim 1 wherein the synthesis gas conversion conditions include a temperature of from about 160° to about 350° C.

20. The process of claim 19 wherein said synthesis gas conversion temperature is from about 175° to about 250° C.

21. The process of claim 1 wherein the total pressure in the synthesis gas conversion zone is from about 1 to about 50 atmospheres.

22. The process of claim 1 wherein the synthesis gas conversion product contains from about 50 to about 65 weight percent hydrocarbons in the $C_9$–$C_{20}$ boiling range.

23. The process of claim 1 wherein said catalyst contains negligible amounts of silicon.

24. The process of claim 1 wherein said catalyst contains less than 5 micromol per gram of impurities creating acid sites.

25. The process of claim 1 wherein said solvent comprises acetone.

26. The process of claim 1 wherein said solvent additionally comprises a lower alcohol.

27. The process of claim 26 wherein said lower alcohol is ethanol.

28. The process of claim 15 wherein said solvent comprises acetone.

29. The process of claim 1 wherein step (B) is conducted at a heating rate of from about 0.5° to about 1° C. per minute up to a maximum hold temperature of from about 190° to about 210° C. for a hold time of from about 16 to about 24 hours and thereafter heating said impregnated alumina support in the presence of hydrogen while heating up to a maximum hold temperature of from about 350° to about 400° C. for a hold time of from about 16 to about 24 hours.

30. The process of claim 29 wherein the second reduction heating step is conducted at the rate of from about 5° to about 10° C. per minute.

* * * * *